United States Patent [19]

Wallace et al.

[11] Patent Number: 4,844,866
[45] Date of Patent: Jul. 4, 1989

[54] CARRIER FOR DETECTING DRUG ABUSE COMPOUNDS

[75] Inventors: Jack E. Wallace; Kenneth Blum, both of San Antonio, Tex.

[73] Assignee: Matrix Technologies, Inc., League City, Tex.

[21] Appl. No.: 670,902

[22] Filed: Nov. 13, 1984

[51] Int. Cl.⁴ .................. G01N 21/78; G01N 33/94
[52] U.S. Cl. .................................. 422/56; 422/57; 436/92; 436/164
[58] Field of Search .................. 436/92, 164, 66; 422/56, 57

[56] References Cited

U.S. PATENT DOCUMENTS

| | | | |
|---|---|---|---|
| 3,761,227 | 9/1973 | Conrad et al. | 436/92 |
| 3,912,655 | 10/1975 | Shukla et al. | 422/56 |
| 3,915,639 | 10/1975 | Friedenberg | 436/901 X |
| 3,955,926 | 5/1976 | Fischer | 422/56 |
| 3,980,434 | 9/1976 | Mertz et al. | 436/92 |
| 4,013,417 | 3/1977 | Raffaele | 436/66 |

FOREIGN PATENT DOCUMENTS

84/02397 6/1984 World Int. Prop. O. .

OTHER PUBLICATIONS

Reimers, Chemical Abstacts, vol. 74, Abstract No. 74:146432s, 1971.
Viala et al., Chemical Abstracts, vol. 85, Abstract No. 85:73030z, 1976.
Ferrara et al., Chemical Abstracts, vol. 88, Abstract No. 88:164984s, 1977.
Sane et al., Chemical Abstracts, vol. 100, Abstract No. 100:56944m, 1983.
Shibasaki et al., Chem. Pharm. Bull., vol. 28, No. 2, pp. 669–672, 1980.
Irs, "Methods of Analysis for Alkaloids, Opiates, Marihuana, Barbiturates & Misc. Drugs", Rev. 6–67, 1967, pp. 52, 53, 61–65.
Jukofsky et al., Journal of Analytical Toxicology, vol. 5, Jan./Feb. 1981, pp. 14–19.

Primary Examiner—Robert J. Hill, Jr.
Attorney, Agent, or Firm—Iver P. Cooper

[57] ABSTRACT

A carrier for detecting drug abuse compounds which changes color upon contact with such compounds. Metabolites of abusable drugs such as natural opiates, i.e., morphine and heroin, are qualitatively and semi-quantitatively detected in physiological fluids by the use of the carrier which has been treated with certain stain-producing components adapted to react with the dug abuse compound residues to form colored products and which may be enhanced by intense light and/or heat.

1 Claim, 1 Drawing Sheet

CARRIER FOR DETECTING DRUG ABUSE COMPOUNDS

BACKGROUND OF THE INVENTION

1. Field of the Invention

This application, in part, relates to methodology for qualitatively detecting the presence of metabolites of natural opiate-type compounds in physiological fluids, particularly human urine. Additionally, it includes a carrier, i.e., a treated paper or dipstick, which has been proven to be especially useful for the qualitative or semi-quantitative analysis of body fluids such as urine or saliva for the presence of drug abuse compound residues.

2. Description of the Prior Art

The need for a rapid qualitative and semi-quantative screening device for the detection of natural opiate-type compounds and resultant metabolites is increasing with the enhanced worldwide utilization of these compounds as well as their structurally similar synthetic analogs. Currently, most of the available analytical procedures for determining opiates in urine are either insufficiently sensitive, unacceptably slow, or involve testing with expensive instruments at a cost that prevents their utilization in situations other than a reference laboratory environment.

The various problems and difficulties in most analytical procedures are clearly recited by Friedenberg in U.S. Pat. No. 3,915,639. Other existing dipstick prior art teachings for detection of various drugs in urine include U.S. Pat. Nos. 3,464,756, 3,468,639, 3,509,872, 3,531,254 and 3,776,114. All show dipsticks for analytical testing of physiological fluids which use an ion exchange material to concentrate the suspected compound. Also, as pointed out in Friedenberg, ". . . in each instance, the range of compounds being tested for is relatively narrow, with uniquely defined chemical properties."

In drug abuse testing, the requirements for detectability are very low and the range of compounds is extremely expansive; a need exists for a method of rapid drug detection which identifies drugs by a simple and direct method not requiring solvent extraction.

SUMMARY OF THE INVENTION

The primary object of this invention is to provide a method and carrier for use in the detection of drugs of abuse in body fluids such as human urine.

Another object is to provide a treated carrier, such as paper or dipstick, which may be in various shapes and sizes, for use in the detection of natural opiate metabolites in human urine.

Still another object is to provide a method and carrier for rapid qualitative identification of metabolites of natural opiate-type compounds.

Another object is to provide a direct qualitative analysis of such drugs of abuse which are present in relatively low concentrations (less than 0.5 micrograms/milliliter) in urine.

Still another object is to provide a direct qualitative analysis wherein false negatives and positives for natural opiate metabolites are significantly reduced.

Other objects and features of the invention will become apparent to those skilled in the art from the following specification when read in the light of the annexed drawings.

BRIED DESCRIPTION OF THE DRAWINGS

DESCRIPTION OF PREFERRED EMBODIMENTS

Figure 1:
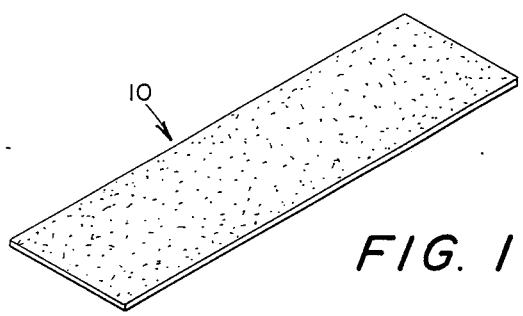
FIG. 1 is a perspective view of a treated strip of paper in accordance with the principles of the subject invention.

Referring now to the drawings, wherein like reference numerals designate like or corresponding parts throughout the several views, there is shown in FIG. 1 a treated paper 10 of desired shape, size, and composition. For purposes of description only and not in limitation, the invention contemplates a carrier wherein at least one component applied thereto is adapted to form a color complex with the drug of interest.

Specifically, one or more plies of porous paper is treated with a 2-6% solution of potassium ferricyanide (2-6 grams/100 milliliter); the solution media is a boric acid-sodium borate buffer at pH 8.8.

Strips of Whatman three millimeter paper, for example, is placed in such buffered potassium ferricyanide solution for one hour, removed, and permitted to air dry. When stored in the absence of light, such dried papers are stable for a period of at lest 4-6 months.

Figure 2:
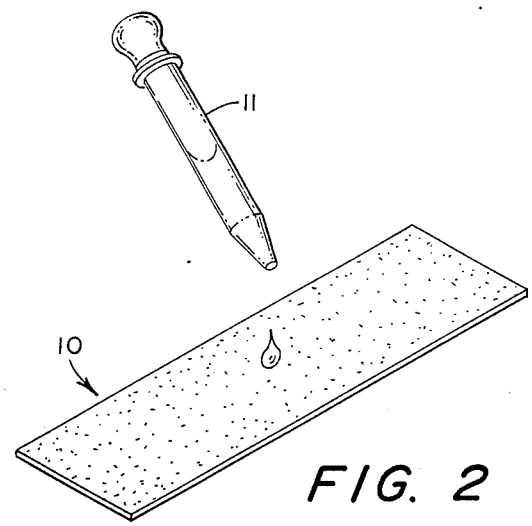
FIG. 2 is a perspective view showing a pipette used to apply a drop of urine or the like onto the surface of the treated paper of FIG. 1.

As shown in FIG. 2 of the drawings, one to five microliters of untreated urine is applied, as by pipette 11 or the like, onto the surface of paper 10, and allowed to at least partially dry. A high intensity light source (not shown) having a wave length in the visible range is then applied to said paper for 5-10 seconds, aiding in the permanent development of the color reaction and making it even more stable than by heating; little or no fading of the test results is evident after seven days. An alternative methodology is to heat paper 10 for 15-30 minutes in an oven heated to 125°-130° Centigrade.

Figure 3:
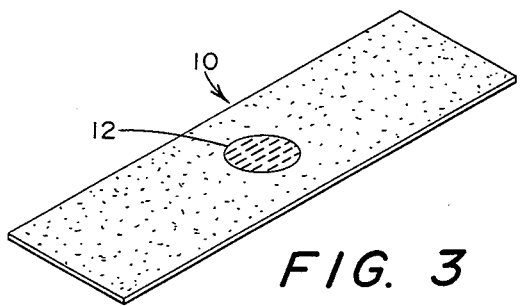
FIG. 3 is a pictorial view showing a urine specimen, after developing, of a negative indication for natural opiate metabolites in human urine.

Referring now to FIG. 3, spot 12 of light gray to white coloration is a negative indication for metabolites of natural opiates and structurally similar synthetic analogs. As viewed in FIG. 4, a spot indicated by reference numeral 13, of a light blue to navy blue coloration, depending upon the concentration of said natural opiates, is a positive color indication for natural opiate metabolites. It is to be understood that a comparison of color may be made between a negative control and the urine specimen being tested.

Figure 4:
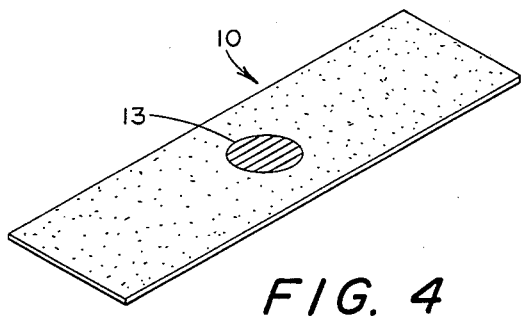
FIG. 4 is a pictorial view showing a urine specimen, after developing, of a positive indication for natural opiate metabolites in human urine.
Figure 5:
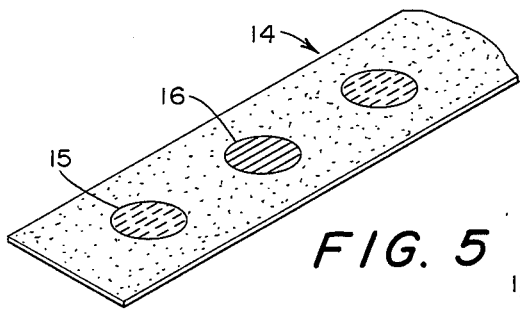
FIG. 5 is a fragmentary, perspective view of an elongated strip of treated paper whereby a plurality of tests are simultaneously conducted.

There is shown in FIG. 4 an elongated strip of paper 14 of desired length treated in the manner heretofore described. Any desired number of untreated urine specimens are conventionally applied to selected portions of said strip of paper, and preferably coded or otherwise marked for identification purposes. Intense heat from a light source or oven in the specified range and for the specified time is then applied to said strip. Spot 15 of light gray to white coloration indicates a negative result for synthetic and natural opiate metabolites whereas spot 16 of light blue to navy blue coloration indicates a positive test for opiate-type compounds. Such strip permits the rapid analytical determination of the presence of synthetic and natural opiates in a large number of urine specimens in a convenient manner.

Figure 6:
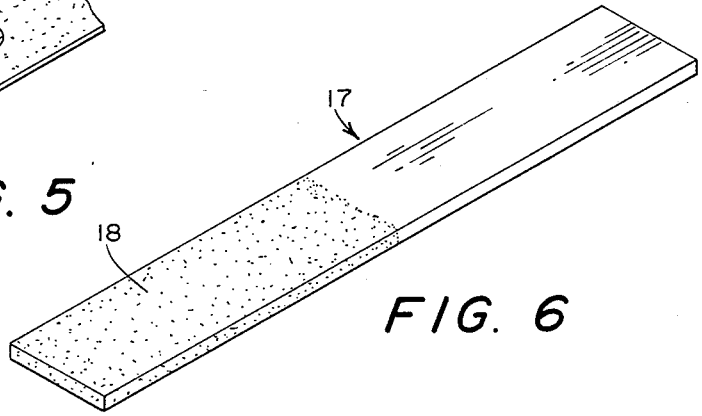
FIG. 6 is a perspective view of a treated dipstick of the subject invention.

Dipstick 17 of FIG. 6, of any suitable shape and size but preferably of elongate, rectangular shape, is composed of wood, other fibrous material, plastic or metal. Any selected portion of said dipstick, preferably the lower end portion indicated by reference numeral 18, is threated in the manner heretofore described in detail.

It is to be understood that the term "natural opieates" used throughout the specification and claims is used in a generic sense and includes methodology and carriers for detecting drug abuse compunds including but not limited to high concentrations of other drugs including amphetamines, pseudoephedrine, cocaine and metabolites of drugs that have a structural entity similar to that of morphine, e.g., atropine, benzotropine, hyoscyamine, dilaudid, normorphine and other synthetic opiates.

TABLE I

| Comparative Analysis of Natural Opiate Testing Methods Utilizing Urine Samples | | |
|---|---|---|
| Method | Total Positives | Total Negatives |
| Standard | 39 | 20 |
| Sample A | 40 (103%) | 19 (95%) |

In the several natural opiate testing methods utilizing urine samples, results of which are shown in Table I, urine specimens were obtained from drug abuse programs in San Antonio, Tex. and its environs.

Well known testing procedures such as the EMIT system (Syva), thin layer chromatography (TLC), and gas liquid chromatography (GLC) were used on the Standard specimens.

Sample A is prepared in accordance with the method and treated carrier of the subject invention. A single drop of untreated urine was placed on said paper and heated at 125°–130° Centigrade for 15–30 minutes. A light blue to navy blue coloration denotes positive for natural opiates whereas a light gray to white coloration indicates a negative for such natural opiates. The numbers in parenthesis indicate the percentage correlation estimated by assigning a value of 100% for the Standard techniques.

The data was systematically evaluated utilizing various statitstical approaches, with the following results:

1. Significant Fisher's exact indicates a rejection of the Null Hypothesis; the Standard procedures (i.e., EMIT, TLC and GLC) and Sample A are independent variables. It may be concluded that the Standard procedures and Sample A are dependent beyond chance ($P<0.001$).

2. The correlation expressed by a contingency coefficient ($C=X^2/N+X^2$), between Sample A and the Standard procedures is $C=0.665$. The estimated percentage correlation for natural opiates in urine samples relative to the Standard procedures is 94.0%.

Interpretation of these data indicate that in a clinical setting there should be no significant different between more expensive and time consuming Standard procedures (EMIT, TLC and GLC) and Sample A of the subject invention in terms of reliability of analysis.

The invention also contemplates other oxidants selected from the group consisting of potassium ferrocyanide, potassium permanganate, cerium sulfate, manganese dioxide, potassium dichromate, chromic oxide, Ninhydrin (triketohydrindene hydrate), and cobalt oxide; said oxidants in the range of 2–6% (2–6 grams/100 milliliters) are conventionally buffered to pH 8.8.

It should be understood, of course, the the foregoing disclosure relates to only preferred embodiments of the invention and that it is intended to cover all changes and modifications of the process and carrier herein chosen for the purposes of the disclosure which do not constitute departures from the spirit and scope of the invention.

What is claimed is:

1. A carrier for testing body fluid specimens to indicate the presence of natural opiates and synthetic analogs of similar chemical structures consisting of a supporting surface, a composition applied to said supporting surface adapted to react with said body fluid specimens to develop an intense color indication for said opiates, said composition comprising a 2–6% solution of potassium ferricyanide buffered in a boric acid-sodium borate solution to pH 8.8.

* * * * *